United States Patent
Allam et al.

(10) Patent No.: US 12,283,392 B2
(45) Date of Patent: Apr. 22, 2025

(54) ELECTRICAL CIRCUIT COMPONENTS MADE FROM SILKWORM SILK WITH SILKWORM-DIGESTED STRUCTURED MATERIALS AND METHODS FOR MANUFACTURING SAME

(71) Applicant: The American University in Cairo, Cairo (EG)

(72) Inventors: Nageh K. Allam, New Cairo (EG); Basant A. Ali, New Cairo (EG)

(73) Assignee: THE AMERICAN UNIVERSITY IN CAIRO, Cairo (EG)

(*) Notice: Subject to any disclaimer, the term of this patent is extended or adjusted under 35 U.S.C. 154(b) by 341 days.

(21) Appl. No.: 17/297,453

(22) PCT Filed: May 5, 2020

(86) PCT No.: PCT/IB2020/054267
§ 371 (c)(1),
(2) Date: May 26, 2021

(87) PCT Pub. No.: WO2020/225733
PCT Pub. Date: Nov. 12, 2020

(65) Prior Publication Data
US 2022/0084712 A1    Mar. 17, 2022

Related U.S. Application Data

(60) Provisional application No. 62/843,830, filed on May 6, 2019.

(51) Int. Cl.
*H01G 11/30* (2013.01)
*A01K 67/35* (2025.01)
(Continued)

(52) U.S. Cl.
CPC .............. *H01B 1/12* (2013.01); *A01K 67/35* (2025.01); *H01B 13/0036* (2013.01);
(Continued)

(58) Field of Classification Search
CPC ... H01B 1/20; H01B 1/22; H01B 1/24; A23K 20/20; A23K 50/90; D02G 3/04;
(Continued)

(56) References Cited

U.S. PATENT DOCUMENTS 9,936,574 B2 * 4/2018 Rogers ................. A61B 5/6867

FOREIGN PATENT DOCUMENTS

| CN | 103898735 A | 9/2015 |
|---|---|---|
| CN | 104878468 A | 9/2015 |

(Continued)

OTHER PUBLICATIONS

English language machine translation of CH 04963015 (pub date 2015).*

(Continued)

*Primary Examiner* — Mark Kopec
(74) *Attorney, Agent, or Firm* — Jenkins, Taylor & Hunt, P.A.

(57) ABSTRACT

A method for manufacturing an electrical circuit component includes preparing a mixture of a structured material and silkworm food. The method further includes feeding the mixture to at least one silkworm. The method further includes harvesting silk produced by the at least one silkworm, wherein the harvested silk includes at least one silkworm silk fiber including silkworm-digested portions of the structured material embedded in or on the at least one fiber. The method further includes incorporating the at least one fiber into an electrical circuit component.

12 Claims, 11 Drawing Sheets

(51) Int. Cl.

| | |
|---|---|
| A23K 20/20 | (2016.01) |
| H01B 1/12 | (2006.01) |
| H01B 13/00 | (2006.01) |
| A23K 20/22 | (2016.01) |
| A23K 50/90 | (2016.01) |
| B82Y 40/00 | (2011.01) |
| D01C 3/02 | (2006.01) |
| D01F 1/09 | (2006.01) |
| D01F 4/02 | (2006.01) |

(52) U.S. Cl.
CPC .............. *H01G 11/30* (2013.01); *A23K 20/22* (2016.05); *A23K 50/90* (2016.05); *B82Y 40/00* (2013.01); *D01C 3/02* (2013.01); *D01F 1/09* (2013.01); *D01F 4/02* (2013.01)

(58) Field of Classification Search
CPC ....... D06M 11/51; H01G 11/26; H01G 11/30; H01G 11/40; H01G 9/042; H01G 9/048
See application file for complete search history.

(56) References Cited

FOREIGN PATENT DOCUMENTS

| | | | | |
|---|---|---|---|---|
| CN | 104963015 | A | 3/2017 | |
| CN | 105023760 | A | 5/2018 | |
| EP | 3955749 | B1 | 2/2025 | |
| TW | 201504490 | A | 2/2015 | |
| WO | WO-2020040697 | A1 * | 2/2020 | ............... H01B 1/04 |

OTHER PUBLICATIONS

Sun et al "Electronic Biomaterials Towards Flexible Sensors: A Review", (2018) Electronic Biomaterials Towards Flexible Sensors: A Review. Biosens Bioelectron Open Acc: BBOA-137. DOI: 10.29011/2577-2260. 100037.*

Zhang et al "Sheath-Core Graphite/Silk Fiber Made by Dry-Meyer-Rod-Coating for Wearable Strain Sensors", ACS Appl. Mater. Interfaces 2016, 8, 20894-20899.*

Ali et al "Silkworms as a factory of functional wearable energy storage fabrics", Scientific Reports (2019) 9:12649.*

Notification of Transmittal of the International Search Report and the Written Opinion of the International Searching Authority, or the Declaration for International Application No. PCT/IB20/54267 (May 5, 2020).

Xu et al., "Obtaining high mechanical performance silk fibers by feeding purified carbon nanotube/lignosulfonate composite to silkworms," RSC Adv, vol. 9, pp. 1-12 (2019).

Ali et al., "Silkworms as a factory of functional wearable energy storage fabrics," Scientific Reports, NatureResearch, vol. 9, No. 12649, pp. 1-8 (2019).

Wang et al., "Carbonized silk georgette as an uultrasensitive wearable strain sensor for full-range human activity monitoring," J. Mater. Chem. C, vol. 5, pp. 1-8 (2017).

Wang et al., "Feeding Single-Walled Carbon Nanotubes or Graphene to Silkworms for Reinforced Silk Fibers," Nano Letters, vol. 16, pp. 6695-6700 (2016).

Cai et al., "Reinforced and Ultraviolet Resistant Silks from Silkworms Fed with Titanium Dioxide Nanoparticles," ACS Sustainable Chemistry & Engineering, vol. 3, pp. 2551-2557 (2015).

Notice of Publication for European Patent Application Serial No. 20802634.4 (Feb. 23, 2022).

Wu, G. H.; Song, P.; Zhang, D. Y.; Liu, Z. Y.; Li, L.; Huang, H. M.; Zhao, H. P.; Wang, N. N.; Zhu, Y. Q., "Robust Composite Silk Fibers Pulled out of Silkworms Directly Fed with Nanoparticles," Int. J. Biol. Macromol. 2017, 104, 533-538.

Yan, J.; Wei, T.; Shao, B.; Ma, F.; Fan, Z.; Zhang, M.; Zheng, C.; Shang, Y.; Qian, W.; Wei, F., "Electrochemical Properties of Graphene Nanosheet/Carbon Black Composites as Electrodes for Supercapacitors," Carbon N. Y. 2010, 48 (6), 1731-1737.

Yin, B.; Zhang, S.; Jiao, Y.; Liu, Y.; Qu, F.; Wu, X., "Facile Synthesis of Ultralong MnO 2 Nanowires as High Performance Supercapacitor Electrodes and Photocatalysts with Enhanced Photocatalytic Activities," CrystEngComm 2014, 16 (43), 9999-10005.

Yu, D.; Kang, G.; Tian, W.; Lin, L.; Wang, W., "Preparation of Conductive Silk Fabric with Antibacterial Properties by Electroless Silver Plating," Appl. Surf. Sci. 2015, 357, 1157-1162.

Yu, M.; Li, J.; Wang, L., "KOH-Activated Carbon Aerogels Derived from Sodium Carboxymethyl Cellulose for High-Performance Supercapacitors and Dye Adsorption," Chem. Eng. J. 2017, 310, 300-306.

Zamarayeva, A. M.; Ostfeld, A. E.; Wang, M.; Duey, J. K.; Deckman, I.; Lechêne, B. P.; Davies, G.; Steingart, D. A.; Arias, A. C., "Flexible and Stretchable Power Sources for Wearable Electronics," Sci. Adv. 2017, 3 (6), e1602051.

Zhang, H.; Ni, M.; Li, F.; Xu, K.; Wang, B.; Hong, F.; Shen, W.; Li, B., "Effects of Feeding Silkworm with Nanoparticulate Anatase TiO2 (TiO2 NPs) on Its Feed Efficiency," Biol. Trace Elem. Res. 2014, 159 (1-3), 224-232.

Ali, B. A.; Metwalli, O. I.; Khalil, A. S. G.; Allam, N. K., "Unveiling the Effect of the Structure of Carbon Material on the Charge Storage Mechanism in MoS 2-Based Supercapacitors," ACS Omega 2018, 3 (11), 16301-16308.

Allam, N. K.; Yen, C.-W.; Near, R. D.; El-Sayed, M. A., "Bacteriorhodopsin/TiO2 Nanotube Arrays Hybrid System for Enhanced Photoelectrochemical Water Splitting," Energy Environ. Sci. 2011, 4 (8), 2909.

Babu, K. M. Silk: Processing, Properties and Applications; 1st Edition, Woodhead Publishing, 2013.

Chawla, K. K., "Foams, Fibers, and Composites: Where Do We Stand?" Mater. Sci. Eng. A 2012, 557 (14). 2-9.

Chen, F.; Liu, X.; Yang, H.; Dong, B.; Zhou, Y.; Chen, D.; Hu, H.; Xiao, X.; Fan, D.; Zhang, C.; et al., "A Simple One-Step Approach to Fabrication of Highly Hydrophobic Silk Fabrics," Appl. Surf. Sci. 2016, 360, 207-212.

Choi, S. H.; Kim, S. W.; Ku, Z.; Visbal-Onufrak, M. A.; Kim, S. R.; Choi, K. H.; Ko, H.; Choi, W.; Urbas, A. M.; Goo, T. W; et al., "Anderson Light Localization in Biological Nanostructures of Native Silk," Nat. Commun. 2018, 9 (1), 1-14.

Chung, D. E.; Kim, H. H.; Kim, M. K.; Lee, K. H.; Park, Y. H.; Um, I. C., "Effects of Different Bombyx Mori Silkworm Varieties on the Structural Characteristics and Properties of Silk," Int. J. Biol. Macromol. 2015, 79, 943-951.

Du, Xuan, et al., "Electrochemical Performances of Nanoparticle Fe3O 4/Activated Carbon Supercapacitor Using KOH Electrolyte Solution," J. Phys. Chem. C 2009, 113 (6), 2643-2646.

Ebrahimi, D.; Tokareva, O.; Rim, N. G.; Wong, J. Y.; Kaplan, D. L.; Buehler, M. J. "Silk—Its Mysteries, How It Is Made, and How It Is Used," ACS Biomater. Sci. Eng. 2015, 1 (10), 864-876.

Gogotsi, Y.; Penner, R. M., "Energy Storage in Nanomaterials—Capacitive, Pseudocapacitive, or Battery-Like?" ACS Nano. 2018, pp. 2081-2083.

Jiang, L.; Zhang, S.; Kulinich, S. A.; Song, X.; Zhu, J.; Wang, X.; Zeng, H., "Optimizing Hybridization of 1T and 2H Phases in MoS 2 Monolayers to Improve Capacitances of Supercapacitors," Mater. Res. Lett. 2015, 3 (4), 177-183.

Kujala, S.; Mannila, A.; Karvonen, L.; Kieu, K.; Sun, Z., "Natural Silk as a Photonics Component: A Study on Its Light Guiding and Nonlinear Optical Properties," Sci. Rep. 2016, 6 (March), 1-9.

Lin, R.; Taberna, P.-L.; Fantini, S.; Presser, V.; Pérez, C. R.; Malbosc, F.; Rupesinghe, N. L.; Teo, K. B. K.; Gogotsi, Y.; Simon, P., "Capacitive Energy Storage from −50 to 100° C Using an Ionic Liquid Electrolyte," J. Phys. Chem. Lett. 2011, 2 (19), 2396-2401.

Liu, B.; Yang, M.; Chen, H.; Liu, Y.; Yang, D.; Li, H., "Graphene-like Porous Carbon Nanosheets Derived from Salvia Splendens for High-Rate Performance Supercapacitors," J. Power Sources 2018, 397, 1-10.

(56) References Cited

OTHER PUBLICATIONS

Liu, M.; Shi, M.; Lu, W.; Zhu, D.; Li, L.; Gan, L., "Core-shell Reduced Graphene Oxide/MnOx@carbon Hollow Nanospheres for High Performance Supercapacitor Electrodes," Chem. Eng. J. 2017, 313, 518-526.

Liu, W. W.; Feng, Y. Q.; Yan, X. Bin; Chen, J. T.; Xue, Q. J., "Superior Micro-Supercapacitors Based on Graphene Quantum Dots," Adv. Funct. Mater. 2013, 23 (33), 4111-4122.

Liu, Z.; Tian, X.; Xu, X.; He, L.; Yan, M.; Han, C.; Li, Y.; Yang, W.; Mai, L., "Capacitance and Voltage Matching between MnO2 nanoflake Cathode and Fe2O3 nanoparticle Anode for High-Performance Asymmetric Micro-Supercapacitors," Nano Res. 2017, 10 (7), 2471-2481.

Ming, J.; Pan, F.; Zuo, B., "Influence Factors Analysis on the Formation of Silk I Structure," Int. J. Biol. Macromol. 2015, 75, 398-401.

Ramadan, M.; Abdellah, A. M.; Mohamed, S. G.; Allam, N. K., "3D Interconnected Binder-Free Electrospun MnO @ C Nanofibers for Supercapacitor Devices," 2018, No. March, 1-8.

Shi, X.; Pei, S.; Zhou, F.; Ren, W.; Cheng, H.-M.; Wu, Z.-S.; Bao, X., "Ultrahigh-Voltage Integrated Micro-Supercapacitors with Designable Shapes and Superior Flexibility," 2018.

Sirichaisit, J.; Brookes, V. L.; Young, R. J.; Vollrath, F., "Analysis of Structure/Property Relationships in Silkworm (*Bombyx mori*) and Spider Dragline (*Nephila edulis*) Silks Using Raman Spectroscopy," Biomacromolecules 2003, 4 (2), 387-394.

Sun, X.; Xie, M.; Wang, G.; Sun, H.; Cavanagh, A. S.; Travis, J. J.; George, S. M.; Lian, J., "Atomic Layer Deposition of TiO 2 on Graphene for Supercapacitors," Jour. Electrochem. Soc. 2012, 159 (4), A364-A369.

Tansil, N. C.; Li, Y.; Teng, C. P.; Zhang, S.; Win, K. Y.; Chen, X.; Liu, X. Y.; Han, M. Y., "Intrinsically Colored and Luminescent Silk," Adv. Mater. 2011, 23 (12), 1463-1466.

Teshome, A.; Raina, S. K.; Vollrath, F., "Structure and Properties of Silk from the African Wild Silkmoth *Gonometa postica* Reared Indoors," J. Insect Sci. 2014, 14 (36), 36.

Vepari, C.; Kaplan, D. L., "Silk as a Biomaterial," Progress in Polymer Science (Oxford). Pergamon Aug. 1, 2007, pp. 991-1007.

Wang, J ; Li, L.; Zhang, M.; Liu, S.; Jiang, L.; Shen, Q., "Directly Obtaining High Strength Silk Fi Ber from Silkworm by Feeding Carbon Nanotubes Author ' s Personal Copy," 2014, 34 (2014), 417-421.

Wang, K.; Meng, Q.; Zhang, Y.; Wei, Z.; Miao, M., "High-Performance Two-Ply Yarn Supercapacitors Based on Carbon Nanotubes and Polyaniline Nanowire Arrays," Adv. Mater. 2013, 25 (10), 1494-1498.

Wen, Z.; Yeh, M. H.; Guo, H.; Wang, J.; Zi, Y.; Xu, W.; Deng, J.; Zhu, L.; Wang, X.; Hu, C.; et al., "Self-Powered Textile for Wearable Electronics by Hybridizing Fiber-Shaped Nanogenerators, Solar Cells, and Supercapacitors," Sci. Adv. 2016, 2 (10), e1600097-e1600097.

European Search Report for European Patent Application Serial No. 20802634.4 (Jul. 14, 2023).

Intent to Grant for European Patent Application Serial No. 20802634.4 (Sep. 2, 2024).

Decision to Grant for European Patent Application Serial No. 20802634.4 (Jan. 16, 2025).

\* cited by examiner

ELECTRICAL CIRCUIT COMPONENTS MADE FROM SILKWORM SILK WITH SILKWORM-DIGESTED STRUCTURED MATERIALS AND METHODS FOR MANUFACTURING SAME

PRIORITY CLAIM

This application claims the priority benefit of U.S. Patent Application Ser. No. 62/843,830, filed May 6, 2019, the disclosure of which is incorporated herein by reference in its entirety.

TECHNICAL FIELD

The subject matter described herein relates to routing traffic to electrical circuit components made from silkworm silk with silkworm-digested structured materials and methods for manufacturing same

BACKGROUND

Natural silk produced by silkworms has been used to make fabrics for thousands of years. More recently, silkworm silk has been used to fabricate biodegradable medical implants, protective fabrics, and biodegradable wearable electronics. However, existing techniques for manufacturing electrical circuit components from silkworm silk require post processing to incorporate functional properties into the silkworm silk and can be non-scalable and/or cost prohibitive.

Accordingly, there exists a need for electrical circuit components made from silkworm silk and methods for manufacturing such components that avoid at least some of the difficulties associated with conventional fabrication of electrical circuit components from silkworm silk.

SUMMARY

An electrical circuit component includes at least one fiber of silkworm silk, the at least one fiber having an outer surface and an interior region bounded by the outer surface. The electrical circuit component includes a plurality of portions of silkworm-digested, structured material located in the interior region or on the outer surface of the at least one fiber, wherein the at least one fiber and the silkworm-digested, structured material have a desired electrical property.

A method for manufacturing an electrical circuit component includes preparing a mixture of a structured material and silkworm food. The method further includes feeding the mixture to at least one silkworm. The method further includes harvesting silk produced by the at least one silkworm, wherein the harvested silk includes at least one silkworm silk fiber including silkworm-digested portions of the structured material embedded in or on the at least one fiber. The method further includes incorporating the at least one fiber into an electrical circuit component.

BRIEF DESCRIPTION OF THE DRAWINGS

The subject matter described herein will now be explained with reference to the accompanying drawings of which.

DETAILED DESCRIPTION

Figure 1A:
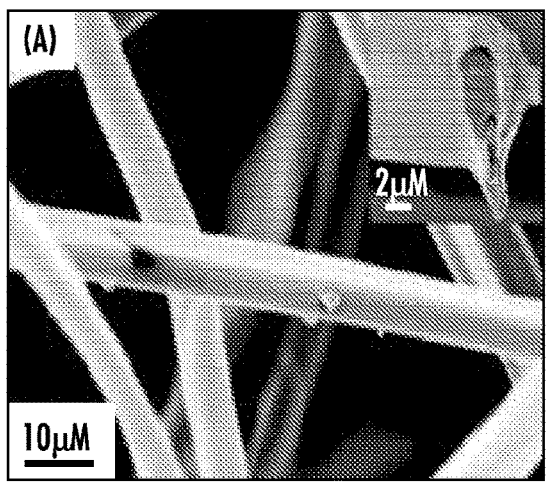
FIG. 1A is a field emission scanning electron microscope (FESEM) image of blank (unmodified) silkworm silk fibers. The blank fibers are referred to hereinafter as S/B fibers.

Feeding *Bombyx mori* larvae with chemically-modified diets affects the structure and properties of the resulted silk. Herein, we provide a road map for the use of silkworms as a factory to produce semiconducting/metallic natural silk that can be used in many technological applications such as supercapacitor electrodes. The silkworms were fed with four different types of chemicals; carbon material (graphite), sulfide ($MoS_2$), oxide ($TiO_2$ nanotubes), and a mixture of reactive chemicals ($KMnO_4/MnCl_2$). All the fed materials were successfully integrated into the resulted silk. The capacitive performance of the resulted silk was evaluated as self-standing fabric electrodes as well as on glassy carbon substrates. The self-standing silk and the silk@glassy carbon substrate showed a great enhancement in the capacitive performance over that of the unmodified counterparts. The specific capacitance of the self-standing blank silk negative and positive electrodes was enhanced 4 and 5 folds at 10 mV/s, respectively upon the modification with $KMnO_4/MnCl_2$ compared to that of the plain silk electrodes.

Metals and semiconductors are the backbone of our modern industry. Therefore, there is a continuous need to develop new methods and technologies to produce such essential materials with the desired characteristics at low cost. Of special interest, enormous efforts have been devoted to develop flexible wearable devices. Those wearable devices are usually made of synthetic nanofibers. However, one of the cheapest and commonly used fibers is the natural silk (NS)[1,2], which has been used, through many decades, as fabric for many applications such as biodegradable medical implants, durable protective fabrics, and eco-friendly wearable electronics.[3-5] NS consists mainly of a polymerized protein known as fibroin covered with a glue-like material named sericin.[6] It is fabricated through the organisms of silkworms from a liquid combination of polymers at room temperature, resulting in a silk that is insoluble in water.[3,7] The fibroin of the *Bombyx mori* larvae is a semi-crystalline biopolymer consisting of glycine, alanine and serine.[8] However, the as-produced spun silks are usually treated with additives to make them functional, which adds to the cost and requires tedious optimization. A promising approach to overcome such obstacles can occur through additives to the food of the silkworms (usually mulberry leaves).[3,8] Feeding the worms with special chemical materials, which can be incorporated in the glands of the worms and mix with the fibroin liquid, is expected to result in a modified-silk composite that comprises the properties of both NS and the incorporated materials.[6-9] The fact that NS radiates heat more than it absorbs and self-cool, makes it a good candidate for electronic applications.[10]

Feeding *Bombyx mori* larvae with nanostructured materials such as CNTs,[7,8] graphene,[7] $TiO_2$[9,11] and other metal oxides[6] have been investigated in recent reports. Details of the feeding process are provided in Appendix A. The feeding process proved that *Bombyx mori* larvae can intake nanostructured materials, which affect the crystallinity of the resulting silk. Feeding the worms with $TiO_2$ was also proved to be nontoxic[11] and even used with bacteria to enhance energy harvesting devices.[12] However, most of the previous reports were limited to the investigation of the mechanical and photonic properties of such modified silk.[7,8] Tailoring the properties of the NS to be used in electronic devices, energy generation, and energy storage devices is yet to be reported. Of special interest, flexible supercapacitors are emerging as promising platforms for energy storage.[13-15]

Herein, we demonstrate the ability to modify the structure and supercapacitive behavior of NS by feeding the *Bombyx mori* larvae with four different types of materials (graphite, $TiO_2$ nanotubes, $MoS_2$, and $KMnO_4/MnCl_2$) for use as supercapacitor electrodes. The study shows that modification of the NS enhanced its capacitive behavior, paving the way for their use in flexible supercapacitor applications.

Results and Discussion

Effect of the Feeding Process

All of the studied silkworms started the feeding on their 5th instar and they did not reject the food. It was observed that the larvae fed with $MoS_2$ were eating more than usual while the ones fed with $KMnO_4/MnCl_2$ were eating in a lower rate than usual. The larvae fed with graphite and $TiO_2$ did not show any unusual behavior in the feeding process. While the cocoons of the blank fed larvae were of homogeneous size and white in color, the chemically-modified ones showed a non-homogenous size and off-white in color. After degumming, all the fabricated fibers were of a clear white color. The resulted silk was given the names S/B, S/G, S/$TiO_2$, S/$MoS_2$ and S/Mn for the blank silk, the graphite modified silk, the $TiO_2$ modified silk, the $MoS_2$ modified silk and the $KMnO_4/MnCl_2$, respectively.

Structure of the Resulted Silk

The morphology of the silk fibers was investigated using FESEM imaging as shown in FIG. 1. Note that the thickness of the fabricated fibers is independent of the type of the chemical additive, having diameters ranging from 9 to 16 µm, in agreement with previous reports.[8,16] The fed materials appeared as debris on the surface of the fibers and/or within their internal fibroins. While the S/B fibers showed a trigonal shaped cross-section as presented in the inset of FIG. 1, the S/G and S/$TiO_2$ showed an oval-shaped cross-section with the additives clearly appearing on the surface of the fibers. However, the S/$MoS_2$ and S/Mn showed a flattened oval cross-section and the fibers were more flat than usual, which may suggest that the additives ($MoS_2$, Mn) were interfered with the fiber materials and reconstructed its protein structure.[8] The elemental composition of the fibers was studied using the EDS technique and the results are presented in Table 1 below. The resulting composition showed that the added material did not exceed 0.03 at % of the total atoms in the fiber, which is an accepted ratio due to the low concentration (0.5 wt % solution) used in the diet. The S/B and S/G did not vary greatly due to the fact that graphite is only made of carbon atoms. However, the S/$MoS_2$ analysis showed 0.03 at % of Mo and 0.05 atom % of S. the S/$TiO_2$ showed a Ti composition of 0.03 at % and the S/Mn showed 0.02 at % of Mn and 0.01 at % of K "from the added KMnO$_4$", with no signal for CI atoms at different positions of the S/Mn fibers indicating that Cl$_2$ gas may have evaporated from the reaction medium during the formation of MnO$_2$.[17] Although the EDS analysis showed a minor ratio of the added materials, the SEM images showed a major effect on the morphology of the resulted fiber. The investigation of the crystal structure of the silk was performed using XRD as presented in FIG. 1(F). The XRD patterns show that all the resulted silk has a mesophase behavior with a broad peak around 20.0°, which can be attributed to the β-sheet of silk II structure.[18-22] Note that the presence of the β-sheet structure is more pronounced in the blank silk and in the S/Mn than in the S/G, S/MoS$_2$ and S/TiO$_2$. The mesophase structure of the silk is believed to facilitate the diffusion of ions to the internal parts of the silk fibers.

Figure 1B:
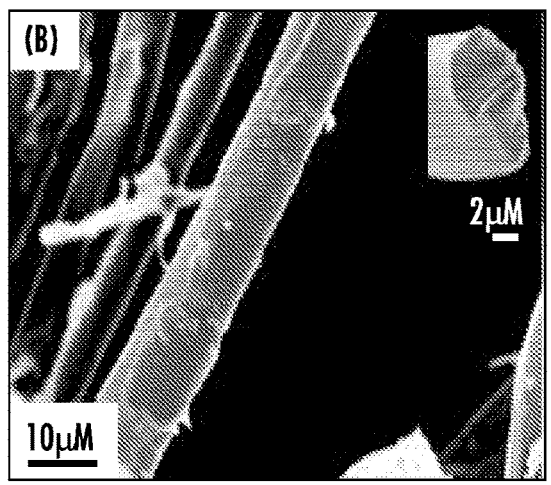
FIG. 1B is an FESEM image of silkworm silk fibers with embedded, silkworm-digested graphite produced by feeding graphite mixed with natural silkworm food to the silkworms. These fibers are referred to hereinafter as S/G fibers.
Figure 1C:
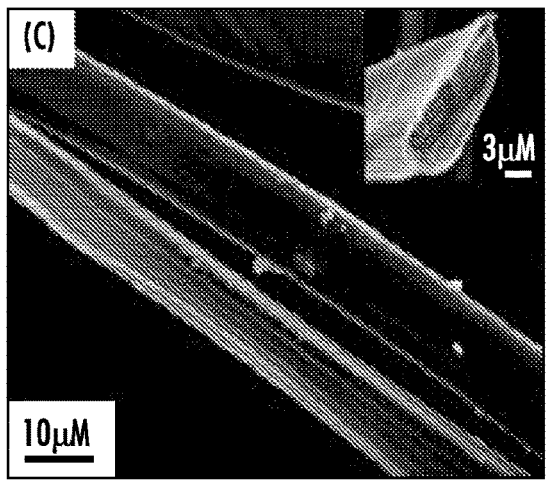
FIG. 1C is an FESEM image of silkworm silk fibers with embedded, silkworm-digested molybdenum disulfide produced by feeding molybdenum disulfide mixed with natural silkworm food to the silkworms. These fibers are referred to hereinafter as $S/MoS_2$ fibers.
Figure 1D:
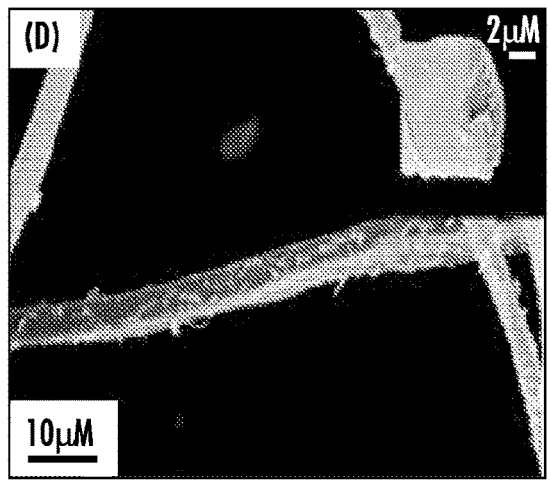
FIG. 1D is an FESEM image of silkworm silk fibers with embedded, silkworm-digested titanium dioxide produced by feeding titanium dioxide mixed with natural silkworm food to the silkworms. These fibers are referred to hereinafter as $S/TiO_2$ fibers.
Figure 1E:
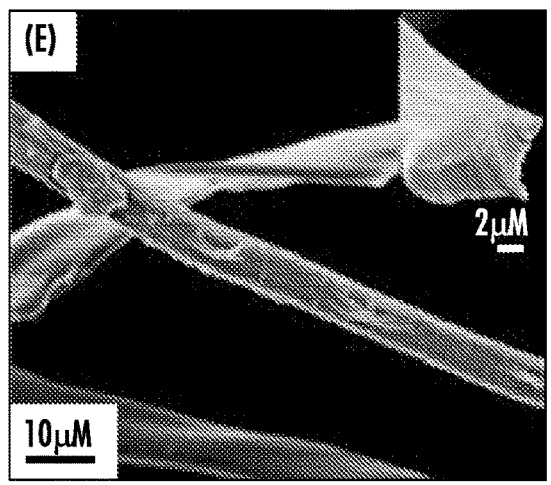
FIG. 1E is an FESEM image of silkworm silk fibers with embedded, silkworm-digested potassium manganate or manganese dichloride ($KMnO_4/MnCl_2$). These fibers are referred to hereinafter as S/M fibers.
Figure 1F:
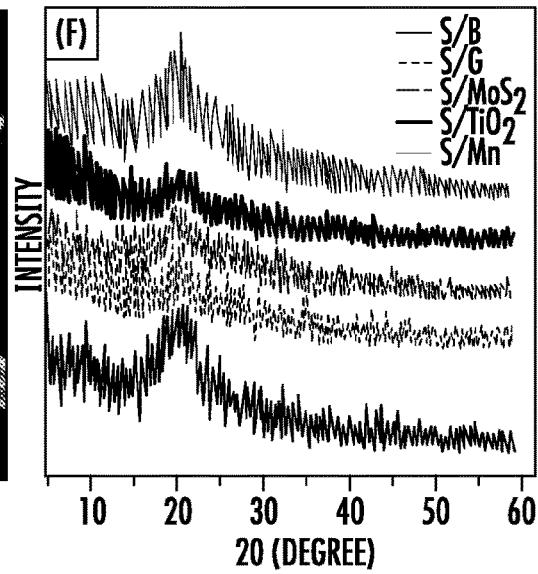
FIG. 1F is a graph of x-ray diffraction patterns of the silk fibers in FIGS. 1A-1E.

FIGS. 1A-1F illustrate results of the morphological and structural analysis of the silk. FIGS. 1A-1E are FESEM images of the fabricated fibers (inset: cross section in the fiber) "pseudo-color is used for clarity" FIG. 1A, S/B; FIG. 1B, S/G; FIG. 1C, S/MoS$_2$; FIG. 1D, S/TiO$_2$; FIG. 1E, S/Mn; and FIG. 1F, the corresponding XRD patterns.

Figure 2A:
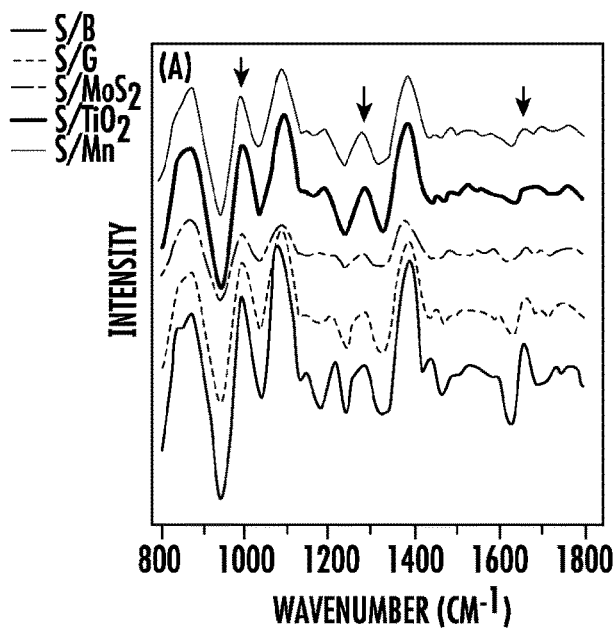
FIG. 2A is a graph of Raman spectra of the modified and unmodified silk fibers from FIGS. 1A-1E.
Figure 2B:
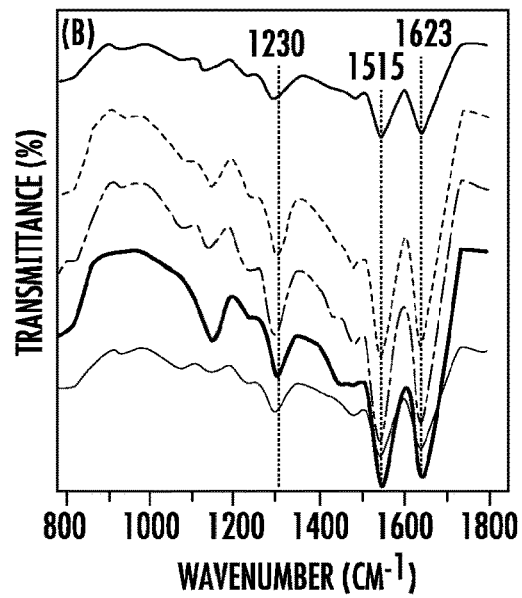
FIG. 2B is a graph of Fourier transform infrared spectra (FTIR) of the modified and unmodified silk fibers from FIGS. 1A-1E.
Figure 2C:
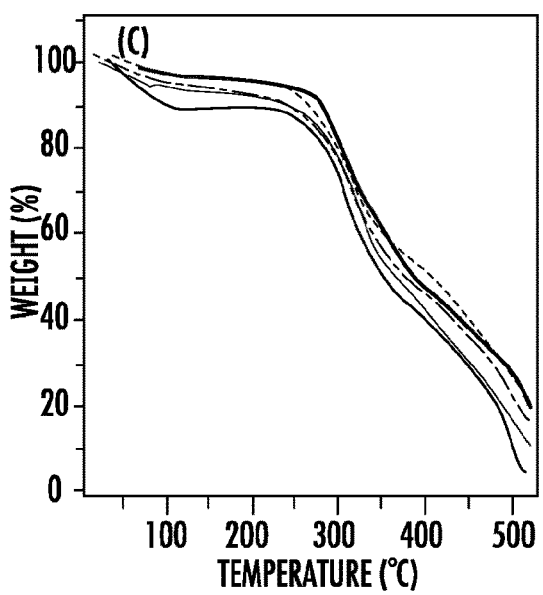
FIG. 2C is a graph of results of thermogravimetric analysis of the modified and unmodified silk fibers from FIGS. 1A-1E showing weight percentage versus temperature of the modified and unmodified silk fibers.

As the Raman spectroscopy has been used as a good tool to investigate the deformation of polymers backbone structure[23], the Raman spectra of the fabricated silk were recorded as shown in FIG. 2A. All fibers showed the same peak position with different intensities, indicating more or less a similar internal structure. The Raman active peaks of the studied fibers are in the range between 800 to 1800 cm$^{-1}$, in a good agreement with literature.[4,23] The observed Raman peaks of the *B. Mori* silk appeared at 1085, 1232 and 1669 cm$^{-1}$ as indicated by arrows in FIG. 2A. The FTIR spectra in FIG. 2B showed the typical peaks at 1623, 1515 and 1230 cm$^{-1}$ characteristic of the silk fibers but with different intensities for different samples.[6,8,9] The peak at 1623 cm$^{-1}$ indicated the presence of amide I structure and the peak is due to the vibration of the C=O bond. The peak at 1515 cm$^{-1}$ indicated the presence of amide II structure and the peak is due to the deformation of the N—H bond in the β sheet structure. The Peak at 1623 cm$^{-1}$ indicated the presence of amide Ill structure and the peak is due to the vibration of the O—C—O bonds and the N—H bond. Thermogravimetric analysis was performed to indicate the thermal stability of the resulted silk fibers. FIG. 2(C) shows that all the silk fibers were stable up to 200° C. then the blank silk started to decompose at ~250° C. The modified silk showed enhanced thermal stability. At 500° C., the remaining weight of the silk was 28.18, 26.7, 21.67, 16.13 and 12.27% for S/TiO$_2$, S/G, S/MoS$_2$, S/Mn, and S/B, respectively.

Electrochemical Performance of the Natural Silk

Figure 7A:
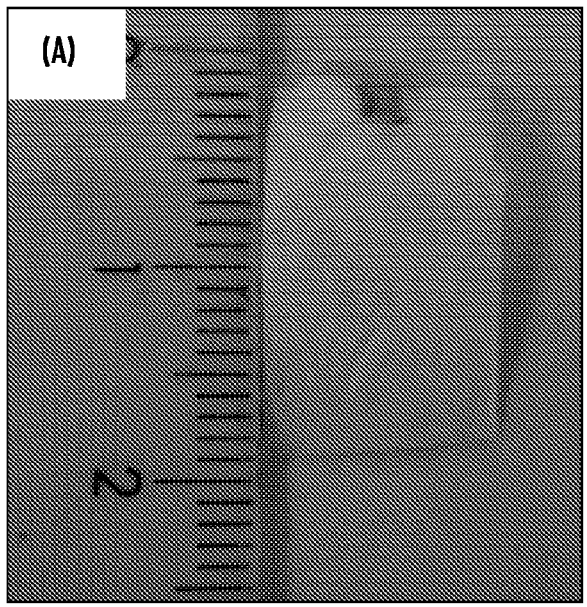
FIGS. 7A and 7B are images of electrodes made from modified silkworm silk using the techniques and materials described herein.
Figure 7B:
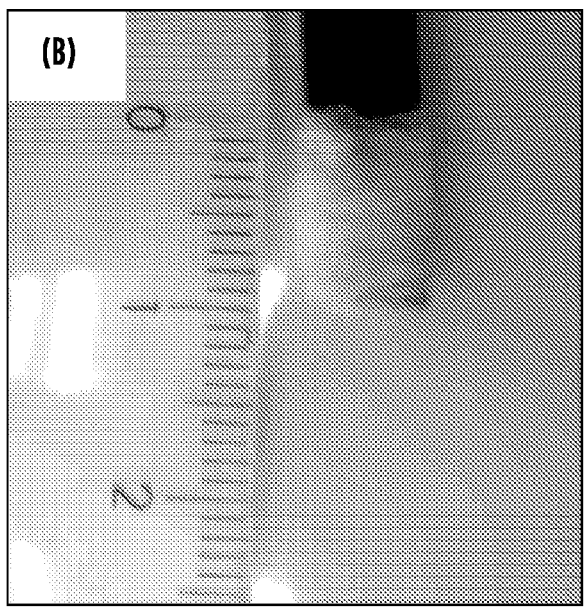

To test the capacitive performance of the natural silk, the self-standing silk was tested once as a positive electrode and once as a negative electrode in a 3-electrode system with 6 M KOH as the electrolyte. Although 6 M KOH is a high concentration electrolyte, it is commonly used with the carbon-based materials in supercapacitor applications.[24-28] Examples of the electrodes produced from the silkworm silk and used in the experiment are shown in FIGS. 7(A) and 7(B).

Figure 3A:
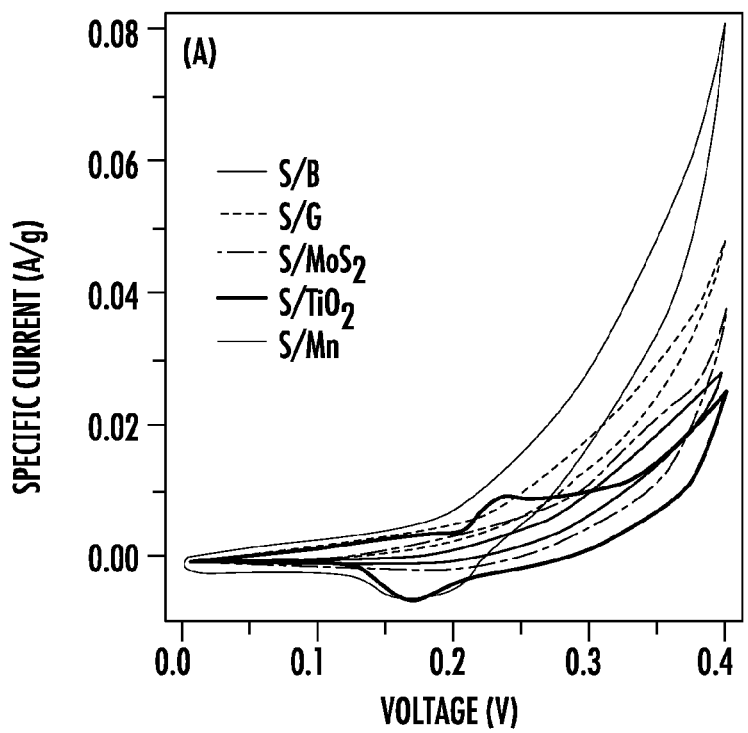
FIG. 3A is a graph of current versus voltage in a positive potential window for self-standing fibers of each of the materials illustrated in FIGS. 1A-1E.
Figure 3B:
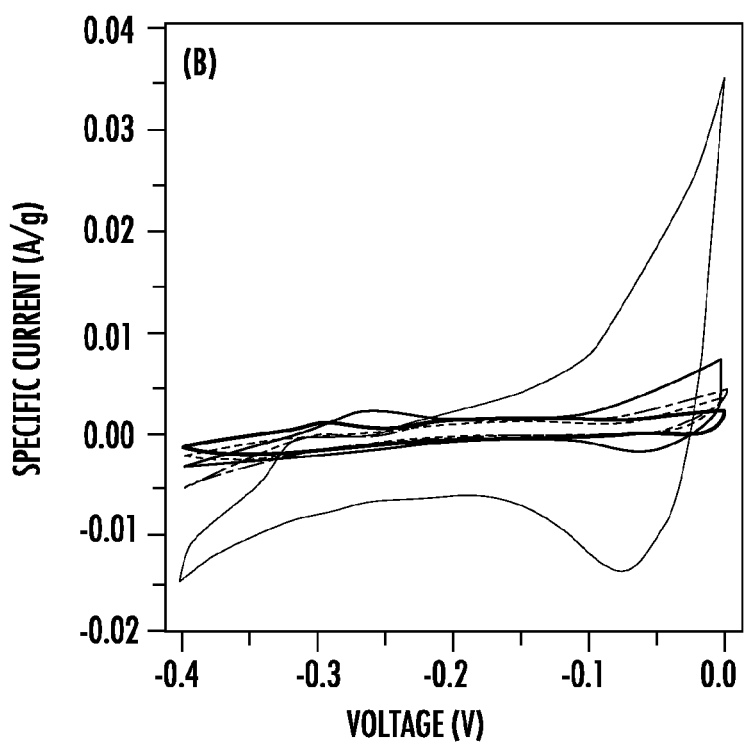
FIG. 3B is a graph of current versus voltage in a negative potential window for self-standing fibers of each of the materials illustrated in FIGS. 1A-1E.
Figure 3C:
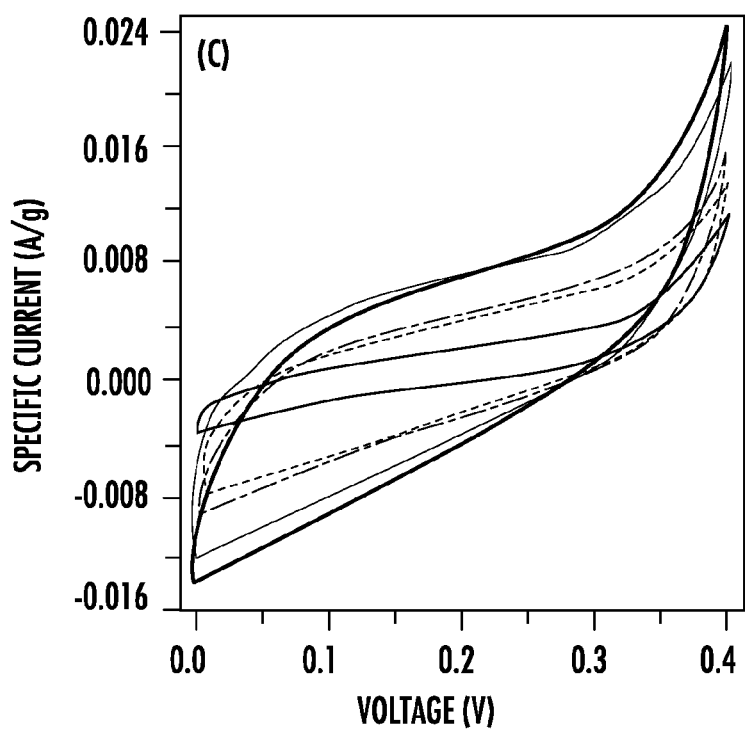
FIG. 3C is a graph of current versus voltage in a positive potential window for fibers of each of the materials illustrated in FIGS. 1A-1E when coiled over a glassy carbon (GC) electrode.
Figure 3D:
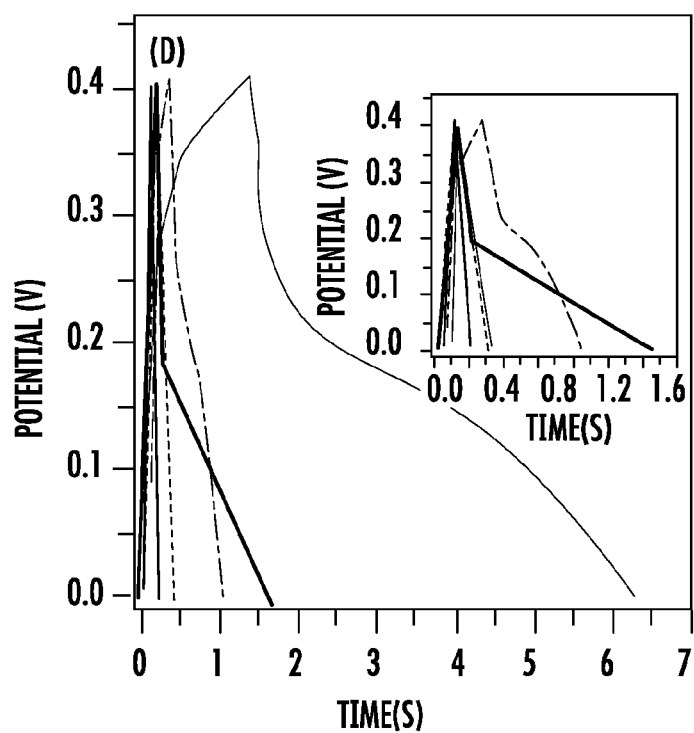
FIG. 3D is a graph of galvanic charge versus discharge (GCD) curves in a positive potential window for self-standing fibers of each of the materials illustrated in FIGS. 1A-1E.
Figure 3E:
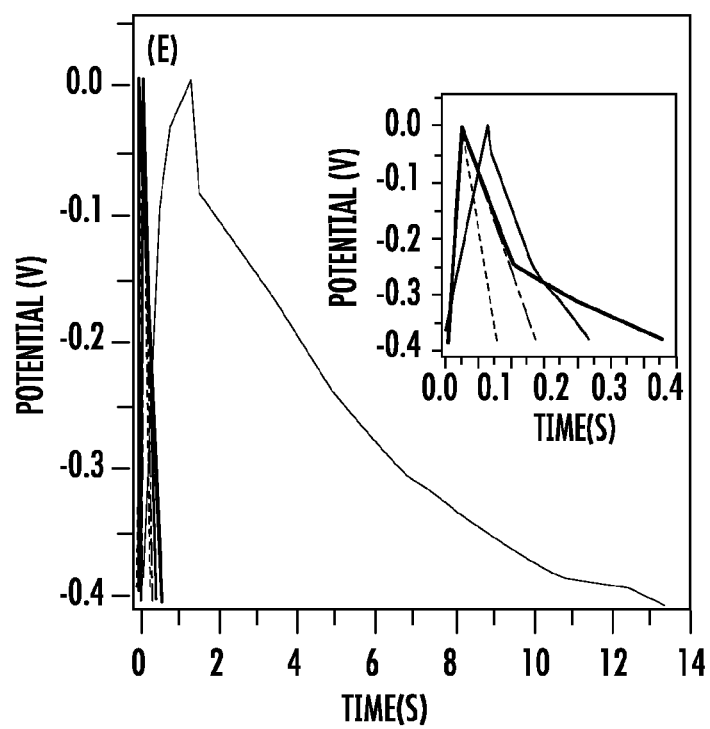
FIG. 3E is a graph of galvanic charge versus discharge (GCD) curves in a negative potential window for self-standing fibers of each of the materials illustrated in FIGS. 1A-1E.
Figure 3F:
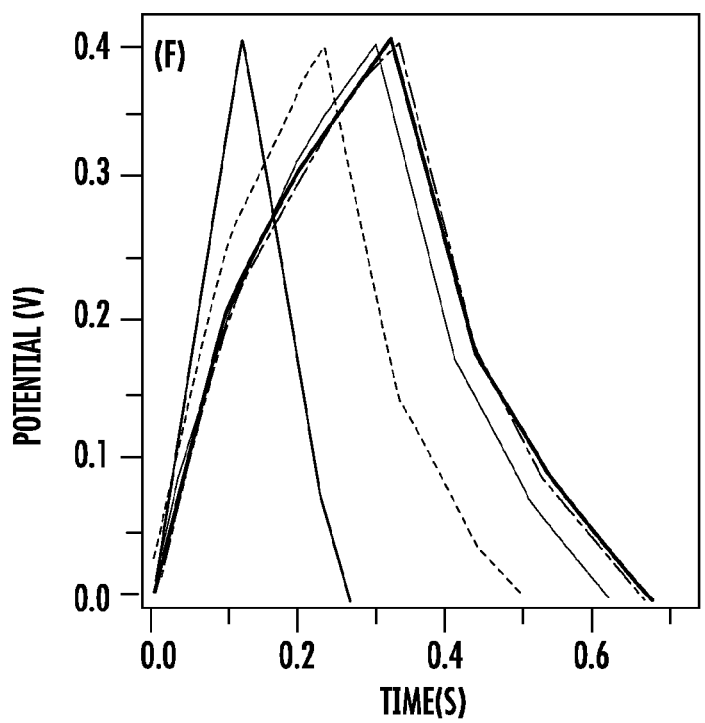
FIG. 3F is a graph of GCD curves in a positive potential window for fibers of each of the materials illustrated in FIGS. 1A-1E when coiled over a GC electrode.

FIGS. 3A-3F illustrate results of the capacitive performance testing. More particularly, FIG. 3A illustrates CVs of the studied self-standing silk fiber at 10 mV/s in positive potential window (inset: legend of FIGS. 3A-3F, FIG. 3B illustrates CVs of the studied self-standing silk fiber at 10 mV/s in negative potential window, FIG. 3C illustrates CVs of the studied silk @ GC at 10 mV/s in positive potential window, FIG. 3D illustrates GCDs of the studied self-standing fibers at 0.1 A/g in positive potential window (inset: enlarged figure), FIG. 3E illustrates GCDs of the studied self-standing fibers at 0.1 Ng in negative potential window (inset: enlarged figure), FIG. 3F illustrates GCDs of the studied silk @ GC at 0.1 Ng in negative potential window.

Usually, the carbon materials show a typical rectangular cyclic voltammogram (CV) reflecting the electrical double layer behaviour (EDL).[29] However, the CVs of the positive and negative silk electrodes in FIGS. 3A and 3B did not show an EDL behavior indicating diffusion processes for the ions in the polymeric structure of the silk.[29] It is expected that the OH$^-$ ion from the KOH reacted with the organic polymer of the silk fibers resulting in a diffusion and pseudocapacitive behavior to the silk electrodes. The ions from the KOH can react with MoS$_2$, TiO$_2$, and MnO$_2$ to give MoSSOH,[30] TiOOK[31] and MnOOK[32], respectively. The CVs of the positive silk electrodes at a scan rate of 10 mV/s (FIG. 3A) show that the redox peaks are more visible in the S/TiO$_2$ while the other additives did not affect the shape of the CV of the S/B. This can be ascribed to the accumulation of TiO$_2$ on the surface of the silk fibers while other additives affected the morphological shape of the silk fibers and did not accumulate with high amount on the surface of the fibers. At a scan rate of 10 mV/s and at a positive potential window, the specific capacitance of the S/Mn showed the highest specific capacitance of 778.975 mF/g while the S/TiO$_2$, S/MoS$_2$, S/G and S/B showed 577.925, 419.767, 247.822, and 157.291 mF/g, respectively. This shows that all the additives dramatically increased the specific capacitance values of silk electrodes. The CVs of the negative silk electrodes at a scan rate of 10 mV/s (FIG. 3B) show clearer redox peaks than the positive electrodes. The specific capacitance of the negative electrodes calculated at a scan rate of 10 mV/s was 1122.832, 263.047, 131.794, 112.141, and 109.403 mF/g for S/Mn, S/B, S/MoS$_2$, S/G and S/TiO$_2$, respectively. To make a deeper study with accurate weight of the active material, the strands of the silk fibers were coiled over a glassy carbon (GC) electrode (see FIG. 7B) and measured as a positive electrode. The calculated specific capacitance of silk fibers @ GC at 10 mV/s (FIG. 3C) showed a capacitance of 610.911, 604.701, 569.047, 556.923, and 206.650 mF/g for S/MoS$_2$, S/TiO$_2$, S/Mn, S/G and S/B, respectively. The contribution of the GC current collector affected the shape of the CVs and shifted them to the EDL rectangular shape. Also, the GC affected the values of the specific capacitance and the order of the materials in their capacitance values. Therefore, the current collector affects greatly the overall performance of the material and we will focus herein on the self-standing fibers as they are more reliable for the study. As one of the most important metrics of supercapacitors is their ability to store and release charges, the time of the charge and discharge was also studied for the silk fibers. FIGS. 3D and 3E show the galvanic charge/discharge (GCD) curves of the self-standing silk fibers at a current density of 0.1 A/g. The GCD curves show a pseudocapacitive behavior.[29] For the positive electrodes, the specific capacitance calculated from the GCD at 0.1 A/g showed the same trend as that calculated from the CVs at 10 mV/s. The specific capacitance values of the positive electrodes calculated at 0.1 A/g were 1222.2, 373.25, 177.2, 54.6, and 29.25 mF/g for S/Mn, S/TiO$_2$, S/MoS$_2$, S/G and S/B, respectively. However, for the negative electrodes, the specific capacitance values calculated at 0.1 A/g were 3114, 108.7, 53.6, 37.05, and 17.8 mF/g for S/Mn, S/TiO$_2$, S/B, S/MoS$_2$ and S/G, respectively. The GCD curves of the silk @ GC positive electrodes at 0.1 A/g are presented in FIG. 3F. The specific capacitance of the positive silk @ GC calculated at 0.1 A/g were 88.3, 85.1, 81.05, 68.1, and 35 mF/g for S/TiO$_2$, S/MoS$_2$, S/Mn, S/G and S/B, respectively. As for the CV results of the silk @ GC, the trend is different, and the effect of the current collector is shifting the shape of the GCD curves to the ideal shape of the EDL capacitor materials. However, the specific capacitance values of the silk with additives are still much higher than this of the blank silk. The CV and GCD results showed that the blank silk (S/B) behaved better as a negative electrode than as a positive electrode and so did the addition of Mn ions (S/Mn) and usually MnO$_2$ acts as a better capacitive material when used as a negative electrode.[17] However, the S/G, S/MoS$_2$ and S/TiO$_2$ enhanced the performance of the silk as a positive electrode than as a negative electrode. Although the amounts of the additives were relatively low, their effect can be attributed to both the nature of the materials and their effect on the morphology of the silk fiber, which controls the diffusion of ions into the silk fibers.

Figure 4A:
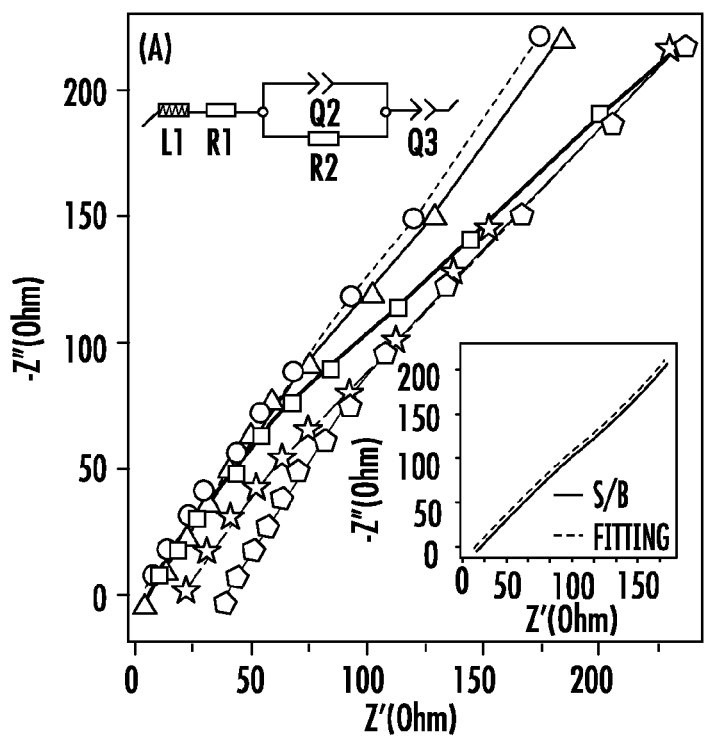
FIG. 4A is a graph of Nyquist plots of 10 mg of each of the types of silk fibers illustrated in FIGS. 1A-1E when coiled over a GC electrode.
Figure 4B:
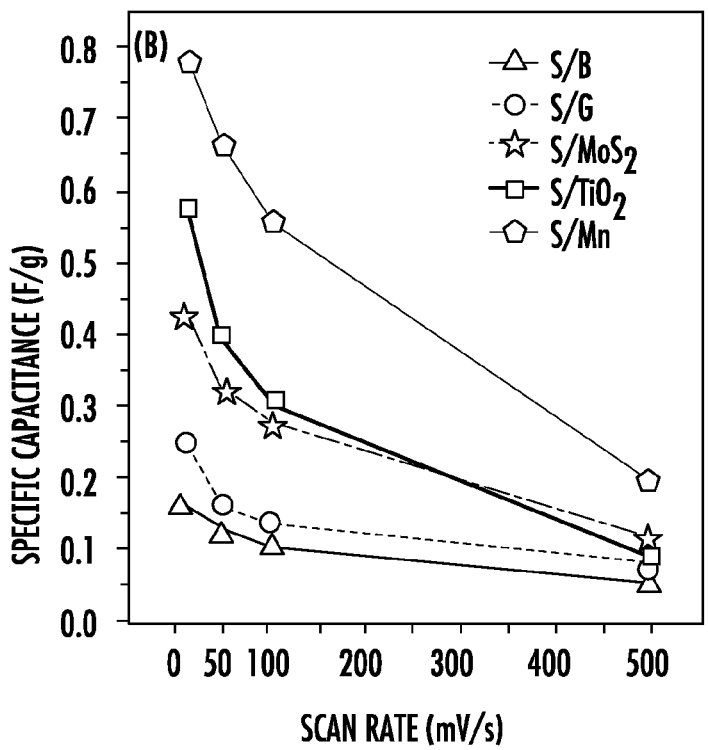
FIG. 4B is a graph of the change in specific capacitance with scan rate for each of the types of silk fibers illustrated in FIGS. 1A-1E for self-standing fibers in a positive potential window.
Figure 4C:
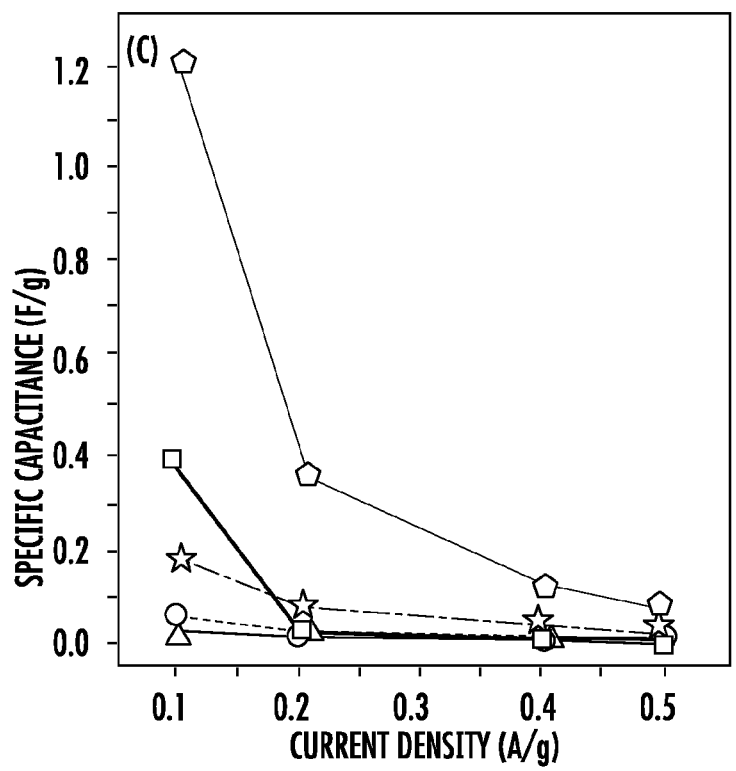
FIG. 4C is a graph of the change in specific capacitance with current density for each of the types of silk fibers illustrated in FIGS. 1A-1E for self-standing fibers in a positive potential window.
Figure 4D:
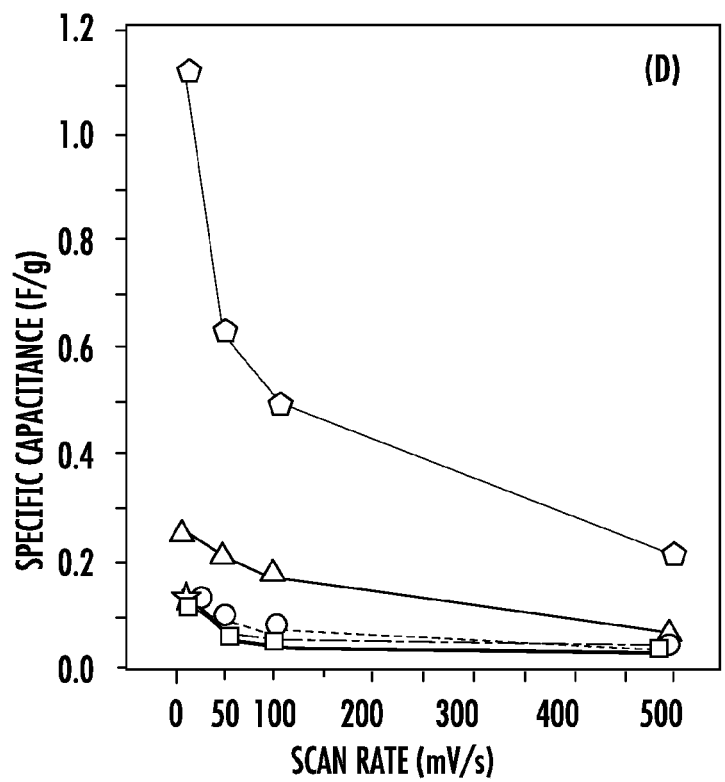
FIG. 4D is a graph of the change in specific capacitance with current density for each of the types of silk fibers illustrated in FIGS. 1A-1E for self-standing fibers in a negative potential window.
Figure 4E:
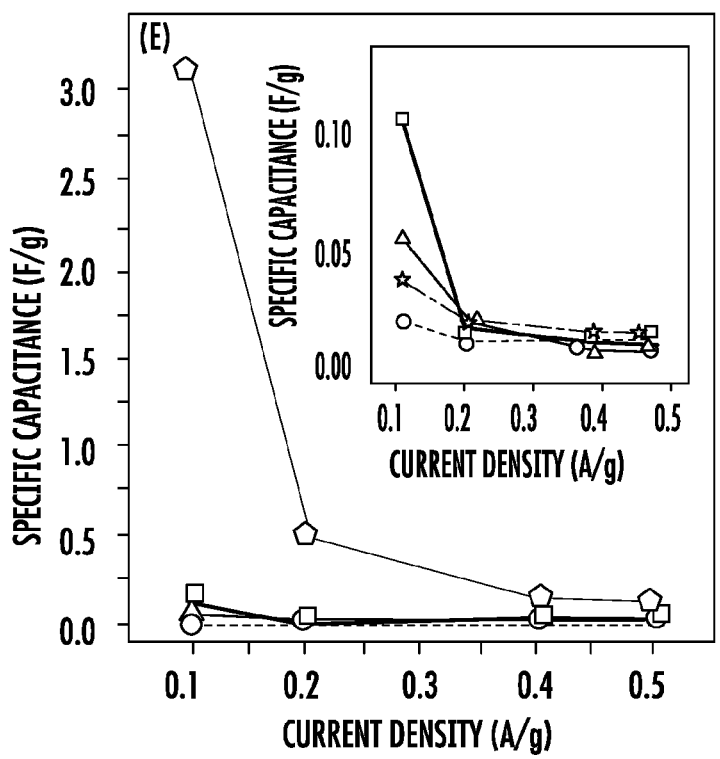
FIG. 4E is a graph of the change in specific capacitance with current density for each of the types of silk fibers illustrated in FIGS. 1A-1E for self-standing fibers in a negative potential window.
Figure 4F:
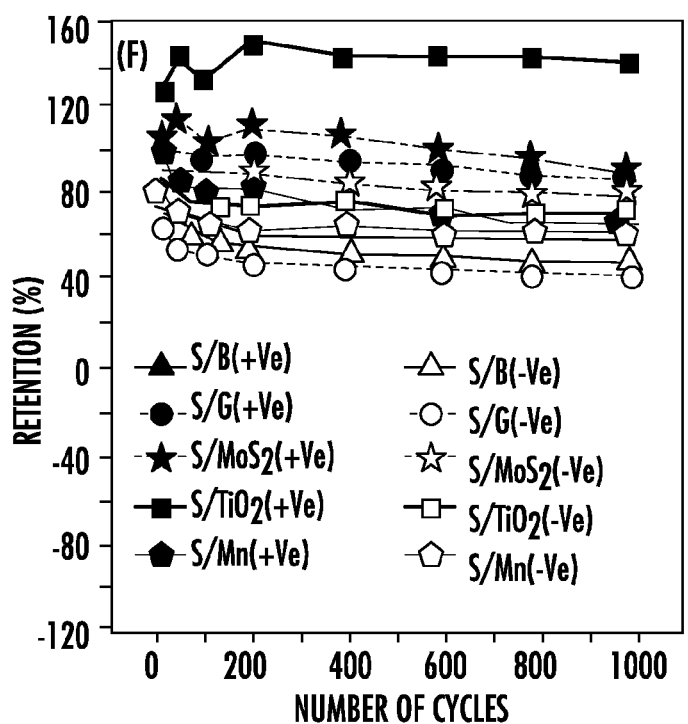
FIG. 4F is a graph illustrating retention percentage versus number of cycles in positive and negative potential windows for self-standing fibers of each of the types illustrated in FIGS. 1A-1E.

FIGS. 4A-4F illustrate results of ectrochemical stability testing of the silk fibers. More particularly, FIG. 4A illustrates Nyquist plots of the studied silk @ GC in the range 1 MHz to 100 mHz (inset: fitting circuit and fitting curve). FIG. 4B illustrates the change in specific capacitance with scan rate (10, 50, 100, and 500 mV/s) for the self-standing fiber in positive potential window (inset: legend for FIGS. 3A-4E). FIG. 4C illustrates the change in specific capacitance with current density (0.1, 0.2, 0.4 1nd 0.5 A/g) for the self-standing fiber in positive potential window. FIG. 4D illustrates the change in specific capacitance with scan rate (10, 50, 100, and 500 mV/s) for the self-standing fiber in negative potential window. FIG. 4E illustrates the change in specific capacitance with current density (0.1, 0.2, 0.4 1nd 0.5 Ng) for the self-standing fiber in negative potential window. FIG. 4F illustrates retention of the studied self-standing fiber in both positive and negative potential window.

The conductivity is one of the main factors that affects the overall performance of a supercapacitor electrode. FIG. 4A shows the Nyquist plots of 10 mg of silk fibers coiled over the same area of a glassy carbon electrode. The resulted curves were fitted to the inset circuit in FIG. 4A, with R$_1$ representing the electrolyte resistance and R$_2$ representing the charge transfer resistance of the material. This circuit showed a perfect match with all the Nyquist plots as presented in the inset of FIG. 4A. The R$_2$ values of the silk fibers were 157.7, 115.7, 104.9, 92.54, and 39.72Ω for S/B, S/G, S/TiO$_2$, S/MoS$_2$ and S/Mn, respectively. Those R$_2$ values show that the additives greatly enhanced the conductivity of the silk fibers and hence enhanced their specific capacitance. The supercapacitors should be able to work under different conditions of scan rates and current densities. The value of the specific capacitance of self-standing silk positive electrodes versus the scan rate is presented in FIG. 4B. Note that the specific capacitance values have the same trend except at 500 mV/s. At 500 mV/s, the specific capacitance values are 196.991, 117.22, 87.491, 76.976, and 55.531 mF/g for S/Mn, S/MoS$_2$, S/TiO$_2$, S/G, S/B, respectively. On the other hand, from the GCD calculations of the positive self-standing silk electrodes (FIG. 4C), the trends differed over the high current density. It showed the values of 78.25, 26.5, 9.5, 8.75, and 5.5 mF/g at 0.5 A/g for S/Mn, S/MoS$_2$, S/G, S/TiO$_2$, and S/B, respectively. For the negative self-standing silk electrodes, the change of specific capacitance with scan rate is presented in FIG. 4D. The values of the S/Mn and S/B were always much higher than those of the S/G, Si/MoS$_2$, and Si/TiO$_2$. At a scan rate of 500 mV/s, the specific capacitance values of the negative self-standing electrodes were 211.009, 60.195, 36.27, 35.729, and 30.272 mF/g for S/Mn, S/B, S/G, S/TiO$_2$, and S/MoS$_2$, respectively. The trend of the specific capacitance at different current densities is presented in FIG. 4E. At a current density of 0.5 A/g, the specific capacitance values of the negative self-standing electrodes were 90.5, 12, 7.75, 6.8, and 5.25 mF/g for S/Mn, S/MoS$_2$, S/G, S/TiO$_2$, and S/B, respectively. Although the S/TiO$_2$, S/MoS$_2$, and S/G specific capacitance values as negative electrode (from GCD) are higher than that of the S/B but it is lower than their positive electrode values (from GCD). Thus, it is believed that S/TiO$_2$, S/MoS$_2$, and S/G act better as positive electrodes than as negative electrodes. Despite the different trends over the different scan rates and current densities, the performance of all silk with additives was better as positive electrodes than the blank silk and the S/Mn was always better as a negative electrode. One of the performance metrics of the supercapacitor materials is their stability upon cycling. FIG. 4F shows the retention percentage of the self-standing silk as positive and negative electrodes over 1000 cycles. The retention fluctuates at the first 200 cycles and reaches a relative stability after 600 cycles. The positive electrodes showed retention of 141.88, 90.59, 87.7, 66.63, and 61.3% for S/TiO$_2$, S/MoS$_2$, S/G, S/Mn, and S/B, respectively after 1000 cycles. The negative electrodes showed retention of 80.99, 67.6, 63.45, 46.06, and 42.13% for S/MoS$_2$, S/TiO$_2$, S/Mn, S/B, and S/G, respectively. From the retention results we conclude that the silk fiber has a better retention as a positive electrode in general and that the additives enhanced the retention and cyclability of the electrodes. the above 100% retention values are attributed to the further diffusion of ions into the material and enhancement of reaction over time.[33,34] Noteworthy to mention that the specific capacitance values in mF are acceptable for self-standing carbon-based materials with no high conductive current collectors.[35-37]

CONCLUSION

We demonstrate the ability to fabricate functionalized natural silk fibers by feeding the silkworms with the material of interest. Specifically, this work highlights the possibility of using natural silk fibers as supercapacitor electrodes upon feeding the worms with high capacitive materials such as graphite, MoS$_2$, TiO$_2$, and KMnO$_4$/MnCl$_2$. The study showed that the fed material did not greatly affect the crystallinity of the silk fibroin and all the added materials enhanced the capacitance performance and the thermal stability of the silk fibers. It was observed that both S/B and S/Mn contained more β-sheet silk, have close thermal stability, and both acted better as negative electrodes. The study proved that natural silk can be tuned for use in energy storage devices.

Exemplary Electrical Circuit Component and Fabrication Process

Figure 5:
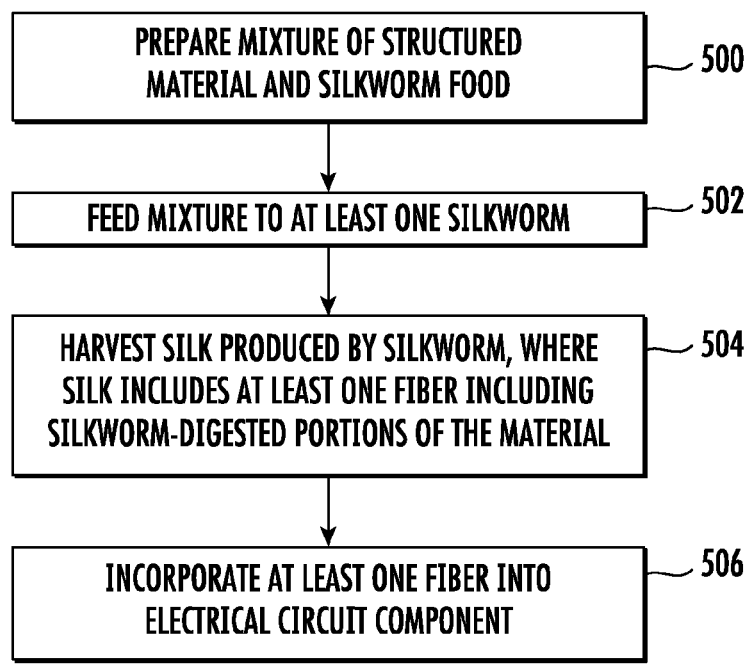
FIG. 5 is a flow chart illustrating an exemplary process for manufacturing an electrical circuit component using modified silkworm silk.

FIG. 5 is an exemplary process for fabricating an electrical circuit component using modified silkworm silk. Referring to FIG. 5, in step 500, a mixture of a structured material and natural silkworm food is prepared. In the examples described above, the structured material may be one or more of graphite, molybdenum disulphide, titanium dioxide, potassium manganate and/or manganese dichloride. One of these materials may be mixed with natural silkworm food, such as mulberry leaves. In some formulations, the structured material may be nanoparticles or nanotubes of the material.

In step 502, the mixture is fed to at least one silkworm. The feeding process is described in detail in Appendix A.

In step 504, silk produced by the silkworm or silkworms is harvested. Details of the harvesting and the processing of the modified silkworm silk after harvesting are provided in Appendix A.

In step 506, the harvested silk is incorporated into an electrical circuit component. In one example, the electrical circuit component may be a positive or negative electrode of a capacitor.

Figure 6:
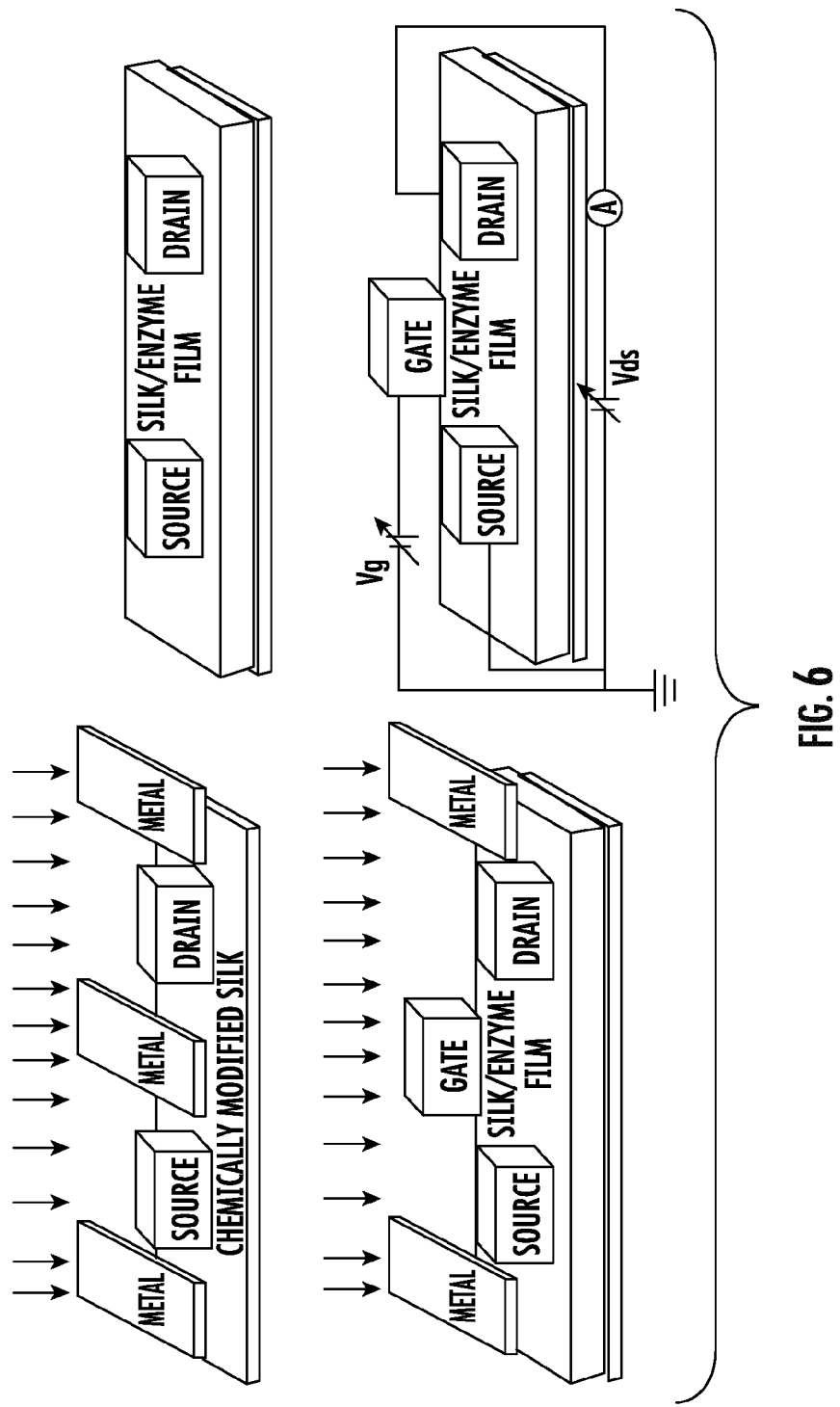
FIG. 6 is a diagram of a wearable sensor made using modified silkworm silk.

FIG. 6 is a diagram of a glucose biosensor and a process of manufacturing the biosensor. In the upper-left quadrant, metal formed on a layer of chemically modified silk is selectively etched away to leave a source and a drain electrode positioned on a silk and enzyme film, as shown in the upper-right figure. The lower left figure shows the deposition of the gate electrode and the etching of remaining metal surrounding the source and drain electrodes. The lower right figure shows the resulting enzymatic biosensor with gate, drain, and source electrodes present on a silk and enzyme film. The silk and enzyme file may be formed of natural silk produced by silkworms fed with materials to embed glucose enzymes in the silk and produce a current flowing from the drain when the silk and enzyme film comes in contact with glucose. The drain current increases with increasing Vds. The drain current can be measured to determine the concentration of glucose in a sample, such as a blood sample.

FIGS. 7A and 7B are images of electrodes formed using silkworm silk modified with one of the above-described materials. In the experiment described above, the silk electrodes were incorporated into a capacitor, and the capacitance was measured. In an alternate example, due to its flexibility and durability, the modified silkworm silk can be incorporated into a garment as part of a wearable sensor.

In one example, the wearable sensor may be a glucose biosensor capable of measuring a wearer's blood glucose level. Glucose biosensors are gaining great interest in medicinal applications due to their benefit in exploring diabetes patients' biological changes. However, enzymatic glucose biosensors are the ones that opened the gate for researchers, since enzymes are highly selective to different substrates. Since wearable flexible and biocompatible materials are the main targets when modifying a biosensor, Natural Silk (NS) will be the most promising material for such applications. NS is not very conducive in nature; our target is to feed the silkworms with a chemically modified diet that will impact in the produced silk fibroin and transform it into conductive silk. The resulted flexible fibers can then be used as a substrate for the enzymatic silk that will bind to the glucose and detect its presence in blood working as a biosensor.

Materials and Methods

Materials

The *Bombyx mori* larvae were brought from a local market in their $3^{rd}$ instar while the study started at the $5^{th}$ instar. The mulberry leaves were also brought from a local market. The graphite with particle size of 150 mesh was purchased from NICE. The $TiO_2$ was prepared as reported[38] through anodization of Ti sheet at 40 V in 0.5 M $HClO_4$ electrolyte. The $MoS_2$ were prepared as reported in our previous work.[39]

A mixture of 1 $KMnO_4$: 16 $MnCl_2$ was used as a possible source for $MnO_2$.[40,41] The KOH used in electrochemical measurements was purchased from AppliChem with purity 85%.

Feeding Process and Silk Preparation

The *B. mori* larvae were divided into 5 groups and each group has 10 larvae and were kept in a transparent dry box with good ventilation. The first group was only feeding on diet of blank mulberry leaves (S/B). While the rest 4 groups were feeding on diet of mulberry leaves previously wetted with solutions of 0.5 wt % graphite (S/G), 0.5 wt % $TiO_2$ (S/$TiO_2$), 0.5 wt % $MoS_2$ (S/$MoS_2$) and 0.5 wt % $KMnO_4$/$MnCl_2$ (S/Mn), respectively. The modified diet started at the worms' $5^{th}$ instar and ended by starting the spinning process. More notes about the feeding process can be found in the Supporting Information. The produced cocoons were degummed before the characterization and the electrochemical measurements. The degumming process included drying the cocoons at 80° C. for 2 hours then the cocoons were immersed in a solution of 0.5 wt % of $Na_2CO_3$ at 100° C. for 30 minutes and this process were repeated 3 times then the cocoons were washed with distilled water for 2 minutes and repeated 3 times.

Characterization of the Produced Silk

The produced silk was characterized using scanning electron microscope (SEM) (FEDEM, Zeiss SEM Ultra 60, 5 kV) the fibers were sputtered with gold at 15 A for 5 minutes before the SEM imaging. The composition of the fibroin was detected using the energy dispersive X-ray analysis (EDX) (JED 2300). The protein signals of the silk fibroin were investigated using a dispersive Raman microscope (Pro Raman-L Analyzer) with an excitation wavelength of 512 nm and Fourier transform infrared spectroscopy (FT-IR) via Perkin Elmer Spectrum One spectrophotometer using KBr pellets. The crystal structure and the change in crystal parameters were investigated using the X-ray powder diffraction (XRD) (Panalytical X'pert PRO MPD X-Diffractometer) with Cu Kα radiation ($\lambda$=0.15418 nm, 40 kV, 30 mA). Thermogravimetric analysis (TGA) was conducted on the natural silk using the device (TGA NETZSCH STA 409 C/CD) at a heating rate of 10° C./min in and a nitrogen flaw rate of 20 ml/min.

Electrochemical Measurements

The capacitive performance of the resulted silk was tested using three-electrode system in which 6 M KOH was used as the electrolyte, coiled Pt as the counter electrode, calomel electrode as the reference electrode and the silk as the working electrode. The silk working electrode was fabricated in two separate methods. To be able to test the performance of the fiber itself, the degummed inner layer of the cocoons was cut into a square of 2*1 $cm^2$ area as presented in FIG. 7A and a drop of Ag paste was used as a current collector on the point of attachment to the alligator clip of the potentiostat. Half the piece of fiber was immersed in the electrolyte and half the weight of the fiber was taken as the weight of the active material in the electrode. Since the electrolyte upwards in the fiber besides the fiber piece was not homogeneous so another method was used to assure the results. The strands of fiber were weighted and coiled over a length of 1 cm of a glassy carbon (GC) rod as presented in FIG. 7B. The part covered with the fiber was immersed completely in the electrolyte and used as the working electrode.

The electrochemical measurements were performed using BioLogic SP-300 potentiostat and included measuring cyclic voltammetry (CV) in potential windows (0.0 to 0.4) and (−0.4 to 0.0) in order to identify the performance of the active materials as positive and negative electrodes respectively. The cyclic voltammetry was measured at different scan rates (10, 50, 100 and 500 mV/s). The capacitance was measured form the cyclic voltammogram using Equation 1. The capacitive performance can also be calculated using Equation 2 from the charge/discharge measurement. The galvanostatic charge/discharge measurement (GCD) was performed at different applied currents (0.1 to 0.5 A/g). The stability of the silk fibers was measured up to 1000 cycle at applied current of 0.1 A/g. The electrochemical impedance spectroscopy (EIS) of the system was measured at frequency range between 1 MHz to 100 mHz. The measurements were repeated twice on two different samples from each type of fibroin.

Notes on the Feeding Process of *B. Mori* Larvae:
1. Keep the larvae in transparent dry box.
2. Leave the mulberry leaves in the solution for 5 minutes then leave it to dry before feeding the worms.
3. Feed the worms 3 times per day.
4. For homogeneous production of silk, try to use mulberry leaves from the same trees.
5. Use wide places equipped with sticks or craters to make it easier for the worm to spin the silk.

Equations:

$$C_s = \frac{\int I\, dV}{vm\, \Delta V} \quad (1)$$

Cs is the specific capacitance, I is the response current density, v is the potential scan rate, $\Delta V$ is the potential window, and m is the mass of electrode material.

$$C_{sp} = \frac{I\, dt}{m\, dV} \quad (2)$$

dt is the discharging time (s), I is the discharging current (A), m is the mass of the active material (g) within the electrode, and dV is the discharging potential range (V).

Tables:

(5) Ebrahimi, D.; Tokareva, O.; Rim, N. G.; Wong, J. Y.; Kaplan, D. L.; Buehler, M. J. Silk—Its Mysteries, How It Is Made, and How It Is Used. *ACS Biomater. Sci. Eng.* 2015, 1 (10), 864-876.

(6) Wu, G. H.; Song, P.; Zhang, D. Y.; Liu, Z. Y.; Li, L.; Huang, H. M.; Zhao, H. P.; Wang, N. N.; Zhu, Y. Q. Robust Composite Silk Fibers Pulled out of Silkworms Directly Fed with Nanoparticles. *Int. J. Biol. Macromol.* 2017, 104, 533-538.

(7) Wang, Q.; Wang, C.; Zhang, M.; Jian, M.; Zhang, Y. Feeding Single-Walled Carbon Nanotubes or Graphene to Silkworms for Reinforced Silk Fibers. *Nano Lett.* 2016, 16 (10), 6695-6700.

(8) Wang, J.; Li, L.; Zhang, M.; Liu, S.; Jiang, L.; Shen, Q. Directly Obtaining High Strength Silk Fi Ber from Silkworm by Feeding Carbon Nanotubes Author's Personal Copy. 2014, 34 (2014), 417-421.

(9) Cai, L.; Shao, H.; Hu, X.; Zhang, Y. Reinforced and Ultraviolet Resistant Silks from Silkworms Fed with Titanium Dioxide Nanoparticles. *ACS Sustain. Chem. Eng.* 2015, 3 (10), 2551-2557.

(10) Choi, S. H.; Kim, S. W.; Ku, Z.; Visbal-Onufrak, M. A.; Kim, S. R.; Choi, K. H.; Ko, H.; Choi, W.; Urbas, A. M.; Goo, T. W.; et al. Anderson Light Localization in Biological Nanostructures of Native Silk. *Nat. Commun.* 2018, 9 (1), 1-14.

(11) Zhang, H.; Ni, M.; Li, F.; Xu, K.; Wang, B.; Hong, F.; Shen, W.; Li, B. Effects of Feeding Silkworm with Nanoparticulate Anatase $TiO_2$ ($TiO2$ NPs) on Its Feed Efficiency. *Biol. Trace Elem. Res.* 2014, 159 (1-3), 224-232.

(12) Allam, N. K.; Yen, C.-W.; Near, R. D.; El-Sayed, M. A. Bacteriorhodopsin/TiO2 Nanotube Arrays Hybrid System for Enhanced Photoelectrochemical Water Splitting. *Energy Environ. Sci.* 2011, 4 (8), 2909.

(13) Wen, Z.; Yeh, M. H.; Guo, H.; Wang, J.; Zi, Y.; Xu, W.; Deng, J.; Zhu, L.; Wang, X.; Hu, C.; et al. Self-Powered Textile for Wearable Electronics by Hybridizing Fiber-Shaped Nanogenerators, Solar Cells, and Supercapacitors. *Sci. Adv.* 2016, 2 (10), e1600097-e1600097.

TABLE 1

| | EDS analysis of the spun silk. | | | | | | | | |
|---|---|---|---|---|---|---|---|---|---|
| Material | C (atom %) | N (atom %) | O (atom %) | Mo (atom %) | S (atom %) | Ti (Atom %) | Mn (atom %) | K (atom %) | Cl (atom %) |
| S/B | 81.94 | 10.31 | 7.75 | N/A | N/A | N/A | N/A | N/A | N/A |
| S/G | 82.24 | 9.84 | 7.92 | N/A | N/A | N/A | N/A | N/A | N/A |
| S/MoS$_2$ | 81.9 | 10.13 | 7.89 | 0.03 | 0.05 | N/A | N/A | N/A | N/A |
| S/TiO$_2$ | 85.96 | 6.86 | 7.15 | N/A | N/A | 0.03 | N/A | N/A | N/A |
| S/Mn | 81.36 | 9.55 | 9.06 | N/A | N/A | N/A | 0.02 | 0.01 | N/A |

The disclosure of each of the following references is hereby incorporated herein by reference in its entirety.

REFERENCES (1) Teshome, A.; Raina, S. K.; Vollrath, F. Structure and Properties of Silk from the African Wild Silkmoth Gonometa Postica Reared Indoors. *J. Insect Sci.* 2014, 14 (36), 36.

(2) Babu, K. M. *Silk: Processing, Properties and Applications;* 1st Edition, Woodhead Publishing, 2013.

(3) Chawla, K. K. Foams, Fibers, and Composites: Where Do We Stand? *Mater. Sci. Eng. A* 2012, 557 (14), 2-9.

(4) Kujala, S.; Mannila, A.; Karvonen, L.; Kieu, K.; Sun, Z. Natural Silk as a Photonics Component: A Study on Its Light Guiding and Nonlinear Optical Properties. *Sci. Rep.* 2016, 6 (March), 1-9.

(14) Zamarayeva, A. M.; Ostfeld, A. E.; Wang, M.; Duey, J. K.; Deckman, I.; Lechêne, B. P.; Davies, G.; Steingart, D. A.; Arias, A. C. Flexible and Stretchable Power Sources for Wearable Electronics. *Sci. Adv.* 2017, 3 (6), e1602051.

(15) Shi, X.; Pei, S.; Zhou, F.; Ren, W.; Cheng, H.-M.; Wu, Z.-S.; Bao, X. Ultrahigh-Voltage Integrated Micro-Supercapacitors with Designable Shapes and Superior Flexibility †‡. 2018.

(16) Vepari, C.; Kaplan, D. L. Silk as a Biomaterial. *Progress in Polymer Science* (Oxford). Pergamon Aug. 1, 2007, pp 991-1007.

(17) Yin, B.; Zhang, S.; Jiao, Y.; Liu, Y.; Qu, F.; Wu, X. Facile Synthesis of Ultralong MnO2 Nanowires as High Performance Supercapacitor Electrodes and Photocata-

(18) Tansil, N. C.; Li, Y.; Teng, C. P.; Zhang, S.; Win, K. Y.; Chen, X.; Liu, X. Y.; Han, M. Y. Intrinsically Colored and Luminescent Silk. *Adv. Mater.* 2011, 23 (12), 1463-1466.
(19) Ming, J.; Pan, F.; Zuo, B. Influence Factors Analysis on the Formation of Silk I Structure. *Int. J. Biol. Macromol.* 2015, 75, 398-401.
(20) Yu, D.; Kang, G.; Tian, W.; Lin, L.; Wang, W. Preparation of Conductive Silk Fabric with Antibacterial Properties by Electroless Silver Plating. *Appl. Surf. Sci.* 2015, 357, 1157-1162.
(21) Chen, F.; Liu, X.; Yang, H.; Dong, B.; Zhou, Y.; Chen, D.; Hu, H.; Xiao, X.; Fan, D.; Zhang, C.; et al. A Simple One-Step Approach to Fabrication of Highly Hydrophobic Silk Fabrics. *Appl. Surf. Sci.* 2016, 360, 207-212.
(22) Chung, D. E.; Kim, H. H.; Kim, M. K.; Lee, K. H.; Park, Y. H.; Um, I. C. Effects of Different *Bombyx Mori* Silkworm Varieties on the Structural Characteristics and Properties of Silk. *Int. J. Biol. Macromol.* 2015, 79, 943-951.
(23) Sirichaisit, J.; Brookes, V. L.; Young, R. J.; Vollrath, F. Analysis of Structure/Property Relationships in Silkworm (*Bombyx Mori*) and Spider Dragline (Nephila Edulis) Silks Using Raman Spectroscopy. *Biomacromolecules* 2003, 4 (2), 387-394.
(24) Xuan, D.; Chengyang, W.; Mingming, C.; Yang, J.; Jin, W. Electrochemical Performances of Nanoparticle Fe3O4/Activated Carbon Supercapacitor Using KOH Electrolyte Solution. *J. Phys. Chem. C* 2009, 113 (6), 2643-2646.
(25) Yan, J.; Wei, T.; Shao, B.; Ma, F.; Fan, Z.; Zhang, M.; Zheng, C.; Shang, Y.; Qian, W.; Wei, F. Electrochemical Properties of Graphene Nanosheet/Carbon Black Composites as Electrodes for Supercapacitors. *Carbon N. Y.* 2010, 48 (6), 1731-1737.
(26) Yu, M.; Li, J.; Wang, L. KOH-Activated Carbon Aerogels Derived from Sodium Carboxymethyl Cellulose for High-Performance Supercapacitors and Dye Adsorption. *Chem. Eng. J.* 2017, 310, 300-306.
(27) Liu, B.; Yang, M.; Chen, H.; Liu, Y.; Yang, D.; Li, H. Graphene-like Porous Carbon Nanosheets Derived from *Salvia Splendens* for High-Rate Performance Supercapacitors. *J. Power Sources* 2018, 397, 1-10.
(28) Liu, M.; Shi, M.; Lu, W.; Zhu, D.; Li, L.; Gan, L. Core-shell Reduced Graphene Oxide/MnOx@carbon Hollow Nanospheres for High Performance Supercapacitor Electrodes. *Chem. Eng. J.* 2017, 313, 518-526.
(29) Gogotsi, Y.; Penner, R. M. Energy Storage in Nanomaterials—Capacitive, Pseudocapacitive, or Battery-Like? *ACS Nano.* 2018, pp 2081-2083.
(30) Jiang, L.; Zhang, S.; Kulinich, S. A.; Song, X.; Zhu, J.; Wang, X.; Zeng, H. Optimizing Hybridization of 1T and 2H Phases in MoS 2 Monolayers to Improve Capacitances of Supercapacitors. *Mater. Res. Lett.* 2015, 3 (4), 177-183.
(31) Sun, X.; Xie, M.; Wang, G.; Sun, H.; Cavanagh, A. S.; Travis, J. J.; George, S. M.; Lian, J. Atomic Layer Deposition of $TiO_2$ on Graphene for Supercapacitors. *J. Electrochem. Soc.* 2012, 159 (4), A364-A369.
(32) Liu, Z.; Tian, X.; Xu, X.; He, L.; Yan, M.; Han, C.; Li, Y.; Yang, W.; Mai, L. Capacitance and Voltage Matching between MnO2 nanoflake Cathode and Fe2O3 nanoparticle Anode for High-Performance Asymmetric Micro-Supercapacitors. *Nano Res.* 2017, 10 (7), 2471-2481.
(33) Ali, B. A.; Metwalli, O. I.; Khalil, A. S. G.; Allam, N. K. Unveiling the Effect of the Structure of Carbon Material on the Charge Storage Mechanism in $MoS_2$-Based Supercapacitors. *ACS Omega* 2018, 3 (11), 16301-16308.
(34) Ramadan, M.; Abdellah, A. M.; Mohamed, S. G.; Allam, N. K. 3D Interconnected Binder-Free Electrospun MnO @ C Nanofibers for Supercapacitor Devices. 2018, No. March, 1-8.
(35) Wang, K.; Meng, Q.; Zhang, Y.; Wei, Z.; Miao, M. High-Performance Two-Ply Yarn Supercapacitors Based on Carbon Nanotubes and Polyaniline Nanowire Arrays. *Adv. Mater.* 2013, 25 (10), 1494-1498.
(36) Liu, W. W.; Feng, Y. Q.; Yan, X. Bin; Chen, J. T.; Xue, Q. J. Superior Micro-Supercapacitors Based on Graphene Quantum Dots. *Adv. Funct. Mater.* 2013, 23 (33), 4111-4122.
(37) Lin, R.; Taberna, P.-L.; Fantini, S.; Presser, V.; Perez, C. R.; Malbosc, F.; Rupesinghe, N. L.; Teo, K. B. K.; Gogotsi, Y.; Simon, P. Capacitive Energy Storage from −50 to 100° C. Using an Ionic Liquid Electrolyte. *J. Phys. Chem. Lett.* 2011, 2 (19), 2396-2401.
(38) Fahim, N. F.; Sekino, T. *Chem. Mater.* 2009, 21, 1967-1979.
(39) Ali, B. A.; Metwalli, O. I.; Khalil, A. S. G.; Allam, N. K. *ACS Omega* 2018, 3, 16301-16308.
(40) Luo, Y.; *Mater. Lett.* 2007, 61, 1893-1895.
(41) Yin, B.; Zhang, S.; Jiao, Y.; Liu, Y.; Qu, F.; Wu, X. *CrystEngComm,* 2014, 16, 9999-10005.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An electrical circuit component comprising:
   at least one fiber of silkworm silk, the at least one fiber having an outer surface and an interior region bounded by the outer surface;
   a plurality of portions of silkworm-digested, structured material located in the interior region or on the outer surface of the at least one fiber, wherein the at least one fiber and the silkworm-digested, structured material have a desired electrical property, wherein the structured material comprises a conductive material that was fed to at least one silkworm and digested by the at least one silkworm; and
   at least one conductor for connecting the at least one fiber to an electrical circuit, wherein the at least one fiber forms a first electrode and further comprising a second electrode and an electrolyte located between the first and second electrodes, wherein the first and second electrodes and the electrolyte form a supercapacitor.

2. The electrical circuit component of claim 1 wherein the at least one fiber comprises a degummed layer cut from a silkworm cocoon.

3. The electrical circuit component of claim 1 wherein the silkworm-digested, structured material comprises a graphite material.

4. The electrical circuit component of claim 1 wherein the silkworm-digested, structured material comprises molybdenum disulfide.

5. The electrical circuit component of claim 1 wherein the silkworm-digested, structured material comprises potassium manganate or manganese dichloride.

6. The electrical circuit component of claim 1 wherein the silkworm-digested, structured material comprises a metal oxide.

7. The electrical circuit component of claim 6 wherein the metal oxide comprises titanium dioxide.

8. The electrical circuit component of claim 1 wherein the desired electrical property is conductivity.

9. The electrical circuit component of claim 1 comprising a glassy carbon (GC) electrode, wherein the at least one silkworm silk fiber comprises a plurality of silkworm silk fibers coiled on a surface of the GC electrode.

10. The electrical circuit component of claim 1 wherein the at least one silkworm silk fiber comprises a plurality of silkworm silk fibers that together form a free-standing electrode.

11. The electrical circuit component of claim 1 comprising a wearable sensor, wherein the at least one silkworm silk fiber comprises a component of the wearable sensor.

12. The electrical circuit component of claim 1 wherein the structured material comprises nanoparticles or nanotubes of the material.

* * * * *